(12) United States Patent
Pierce et al.

(10) Patent No.: US 6,730,054 B2
(45) Date of Patent: May 4, 2004

(54) BLOOD COLLECTION SYSTEMS AND METHODS THAT DERIVE ESTIMATED EFFECTS UPON THE DONOR'S BLOOD VOLUME AND HEMATOCRIT

(75) Inventors: Jennifer A Pierce, Arlington Heights, IL (US); Timothy J Patno, Evanston, IL (US); Robert Cairone, Crystal Lake, IL (US); John T Foley, Wheeling, IL (US)

(73) Assignee: Baxter International Inc., Deerfield, IL (US)

( * ) Notice: Subject to any disclaimer, the term of this patent is extended or adjusted under 35 U.S.C. 154(b) by 57 days.

(21) Appl. No.: 09/789,183

(22) Filed: Feb. 20, 2001

(65) Prior Publication Data

US 2002/0062100 A1 May 23, 2002

Related U.S. Application Data

(63) Continuation-in-part of application No. 09/419,742, filed on Oct. 16, 1999.

(51) Int. Cl.$^7$ ............................................. A61M 37/00
(52) U.S. Cl. ..................... 604/6.01; 604/6.11; 604/5.01
(58) Field of Search ................. 210/646, 781, 210/782; 604/4.01, 5.01, 6.01–6.07, 6.11

(56) References Cited

U.S. PATENT DOCUMENTS

| | | | |
|---|---|---|---|
| 4,479,761 A | * | 10/1984 | Bilstad et al. ............... 417/395 |
| 5,178,603 A | * | 1/1993 | Prince ........................ 604/6.01 |
| 5,496,265 A | | 3/1996 | Langley et al. |
| 5,549,834 A | | 8/1996 | Brown |
| 5,581,687 A | | 12/1996 | Lyle et al. |
| 5,653,887 A | | 8/1997 | Wahl et al. |
| 5,658,240 A | | 8/1997 | Urdahl et al. |
| 5,681,272 A | | 10/1997 | Lee |
| 5,690,835 A | | 11/1997 | Brown |
| 5,712,798 A | | 1/1998 | Langley et al. |
| 5,730,883 A | | 3/1998 | Brown et al. |
| 5,738,796 A | * | 4/1998 | Bormann et al. ........... 210/806 |
| 5,769,811 A | * | 6/1998 | Stacey et al. ............... 604/4.01 |
| 5,795,317 A | * | 8/1998 | Brierton et al. ............ 604/6.05 |
| 5,970,423 A | | 10/1999 | Langley et al. |
| 6,071,421 A | | 6/2000 | Brown |
| 6,113,554 A | * | 9/2000 | Gilcher et al. .............. 600/573 |
| 6,200,287 B1 | | 3/2001 | Keller et al. |
| 6,233,525 B1 | | 5/2001 | Langley et al. |
| 6,256,643 B1 | | 7/2001 | Cork et al. |
| 6,319,471 B1 | | 11/2001 | Langley et al. |

* cited by examiner

*Primary Examiner*—Angela D. Sykes
*Assistant Examiner*—Leslie R. Deak
(74) *Attorney, Agent, or Firm*—Daniel D. Ryan; Bradford R. L. Price

(57) ABSTRACT

Blood processing systems and methods convey blood drawn from a donor through a blood processing circuit to separate the blood into at least one targeted blood component for collection. The systems and methods derive an estimated effect of the procedure upon the donor. The estimated effect can be expressed in terms of a net blood fluid volume loss, or as a hematocrit of the donor after completion of the desired blood collection procedure. The systems and methods present the estimated effect to an operator for viewing, reading, or offloading.

30 Claims, 7 Drawing Sheets

BLOOD COLLECTION SYSTEMS AND METHODS THAT DERIVE ESTIMATED EFFECTS UPON THE DONOR'S BLOOD VOLUME AND HEMATOCRIT

RELATED APPLICATION

This application is a continuation-in-part of U.S. patent application Ser. No. 09/419,742, filed Oct. 16, 1999, and entitled "Automated Collection Systems and Methods for Obtaining Red Blood Cells, Platelets, And Plasma From Whole Blood," which is incorporated herein by reference.

FIELD OF THE INVENTION

The invention relates to centrifugal blood processing systems and apparatus.

BACKGROUND OF THE INVENTION

Certain therapies transfuse large volumes of blood components. For example, some patients undergoing chemotherapy require the transfusion of large numbers of platelets on a routine basis. Manual blood bag systems simply are not an efficient way to collect these large numbers of platelets from individual donors.

On line blood separation systems are today used to collect large numbers of platelets to meet this demand. On line systems perform the separation steps necessary to separate concentration of platelets from whole blood in a sequential process with the donor present. On line systems establish a flow of whole blood from the donor, separate out the desired platelets from the flow, and return the remaining red blood cells and plasma to the donor, all in a sequential flow loop.

Large volumes of whole blood (for example, 2.0 liters) can be processed using an on line system. Due to the large processing volumes, large yields of concentrated platelets (for example, $4 \times 10^{11}$ platelets suspended in 200 ml of fluid) can be collected.

Nevertheless, a need still exists to further improve systems and methods for collecting cellular-rich concentrates, like red blood cells, from blood components, in a way that lends itself to use in high volume, on line blood collection environments, where higher yields of critically needed cellular blood components like platelets and red blood cells can be realized.

SUMMARY OF THE INVENTION

The invention provides blood processing systems and methods that separate blood drawn from a donor through a blood processing circuit to perform a desired blood collection procedure. During the procedure, a volume of the targeted blood component is collected. The systems and methods derive an estimated effect of the procedure upon the donor. The systems and methods present the estimated effect to an operator.

According to one aspect of the invention, the estimated effect is expressed in terms of a net blood fluid volume loss. In one embodiment, the estimated effect takes into account blood loss due to the volume of targeted blood component collected and a residual fluid volume of the blood processing circuit. In one embodiment, a volume of replacement fluid is conveyed to the donor during the desired blood collection procedure, and the estimated effect takes into account the volume of replacement fluid conveyed to the donor. In one embodiment, the estimated effect expresses the net blood fluid volume loss as a percentage of a blood volume of the donor that existed prior to the desired blood processing procedure. In one embodiment, the estimated effect expresses the net blood fluid volume loss as a percentage of weight of the donor.

According to another aspect of the invention, the estimated effect is expressed in terms of a hematocrit of the donor after completion of the desired blood collection procedure.

According to either aspect of the invention, blood can be conveyed through the blood processing circuit to collect a volume of red blood cells, or a volume of platelets, a volume of plasma, or combinations thereof. In one embodiment, in a first mode, platelets are collected while returning red blood cells to the donor and, in a second mode, platelets and red blood cells are collected without returning platelets or red blood cells to the donor.

According to either aspect of the invention, the estimated effect can be presented in a visual display, or in printed form, or in a data form suitable for offloading, or combinations thereof.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims. The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figure 1:
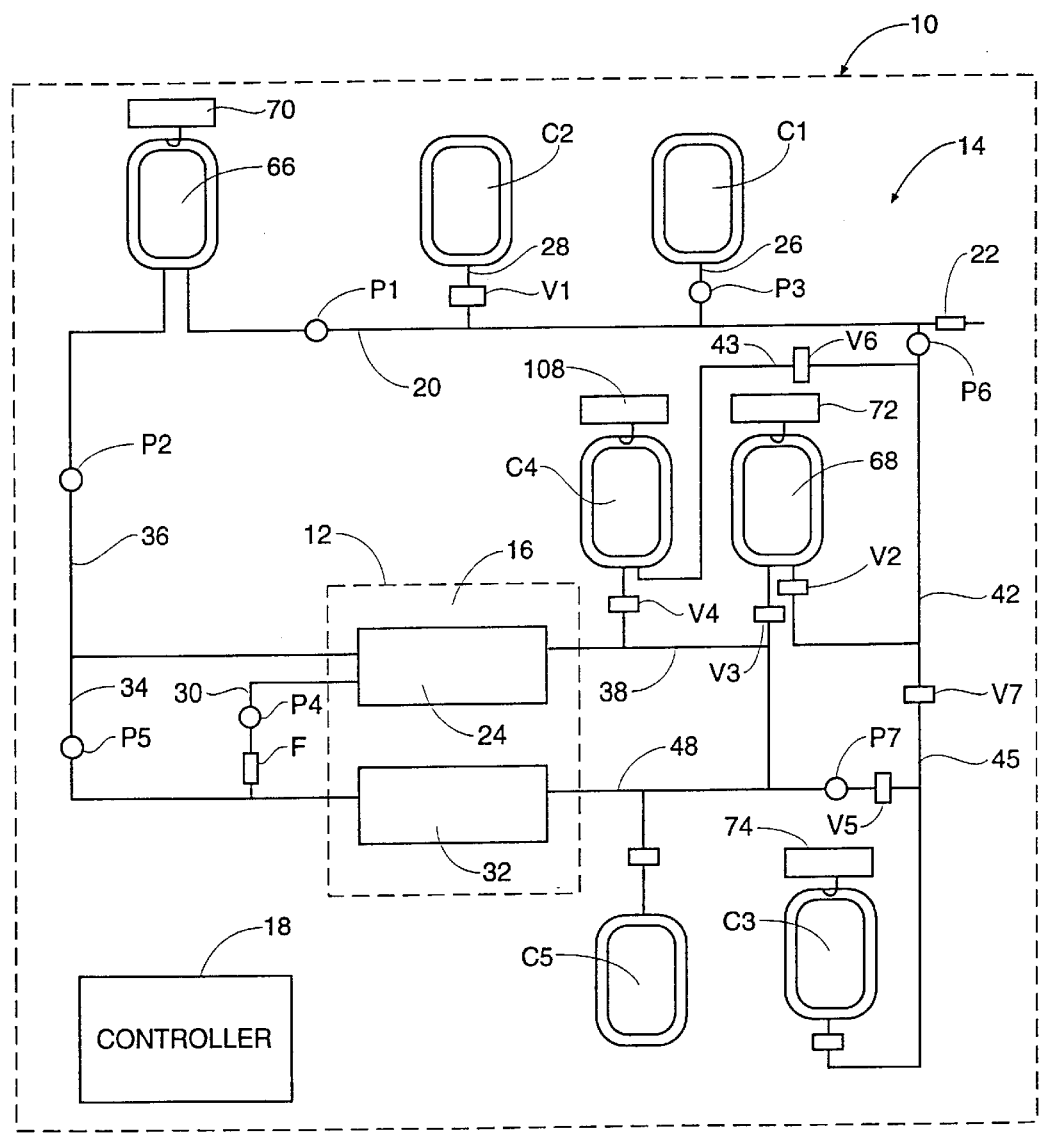
FIG. 1 is a diagrammatic view of an on-line blood processing system.

FIG. 1 shows in diagrammatic form an on line blood processing system 10 for carrying out an automated blood collection procedure.

As illustrated, the system 10 comprises a single needle blood collection network, although a double needle network could also be used.

I. System Overview

The system 10 includes an arrangement of durable hardware elements, whose operation is governed by a processing controller 18. The hardware elements include a centrifuge 12, in which whole blood (WB) from a donor is separated into platelets, plasma, and red blood cells. A representative centrifuge that can be used is shown in Brown et al U.S. Pat. No. 5,690,602, which is incorporated herein by reference.

The hardware elements will also include various pumps, which are typically peristaltic (designated P1 to P7); and various in line clamps and valves (designated V1 to V7). Of course, other types of hardware elements may typically be present, which FIG. 1 does not show, like solenoids, pressure monitors, and the like.

The system 10 typically also includes some form of a disposable fluid processing assembly 14 used in association with the hardware elements. In the illustrated embodiment, the assembly 14 includes a processing chamber 16 having two stages 24 and 32. In use, the centrifuge 12 rotates the processing chamber 16 to centrifugally separate blood components.

The construction of the two stage processing chamber 16 can vary. For example, it can take the form of double bags, like the processing chambers shown and described in Cullis et al. U.S. Pat. No. 4,146,172, which is incorporated herein by reference. Alternatively, the processing chamber 16 can take the form of an elongated two stage integral bag, like that shown and described in Brown U.S. Pat. No. 5,632,893, which is also incorporated herein by reference.

In the illustrated blood processing system 10, the processing assembly 14 also includes an array of flexible tubing that forms a fluid circuit. The fluid circuit conveys liquids to and from the processing chamber 16. The pumps P1–P7 and the valves V1–V7 engage the tubing to govern the fluid flow in prescribed ways. The fluid circuit further includes a number of containers (designated C1 to C5) to dispense and receive liquids during processing.

A controller 18 governs the operation of the various hardware elements to carry out one or more processing tasks using the assembly 14. The controller 18 also performs real time evaluation of processing conditions and outputs information to aid the operator in maximizing the separation and collection of blood components.

The system 10 can be configured to accomplish diverse types of blood separation processes. FIG. 1 shows the system 10 configured to carry out an automated procedure using a single needle 22 to collect from a single donor (i) a desired yield of concentrated platelets suspended in plasma (PC) (e.g., upwards to two therapeutic units), which (if desired) can be provided essentially free of leukocytes, (ii) a desired volume of concentrated red blood cells (RBC) (e.g., upwards to about 200 ml at a hematocrit of about 100% or upwards to about 230 ml at a hematocrit of about 85%), which (if desired) can also be provided essentially free of leukocytes, and (iii) a desired volume (if desired) of platelet-poor plasma (PPP).

The system 10 can collect various volumes of PC, PPP, and RBC products as governed by applicable regulations for allowable blood volumes. For example, in the United States, component volume iterations that the system 10 can presently provide include, e.g.:(i) one therapeutic unit each of PC, PPP, and RBC, or (ii) one therapeutic unit each of PC and RBC, or (iii) two therapeutic units of PC and one unit of RBC.

Further details of the operation of the system 10 to achieve these blood processing objectives will be described later.

II. The System Controller

The controller 18 carries out the overall process control and monitoring functions for the system 10 as just described.

In the illustrated and preferred embodiment (see FIG. 2), the controller comprises a main processing unit (MPU) 44. In the preferred embodiment, the MPU 44 comprises a type 68030 microprocessor made by Motorola Corporation, although other types of conventional microprocessors can be used.

In the preferred embodiment, the MPU 44 employs conventional real time multi-tasking to allocate MPU cycles to processing tasks. A periodic timer interrupt (for example, every 5 milliseconds) preempts the executing task and schedules another that is in a ready state for execution. If a reschedule is requested, the highest priority task in the ready state is scheduled. Otherwise, the next task on the list in the ready state is schedule.

A. Hardware Control

The MPU 44 includes an application control manager 46. The application control manager 46 administers the activation of a library 48 of control applications. Each control application prescribes procedures for carrying out given functional tasks using the system hardware (e.g., the centrifuge 12, the pumps P1–P7, and the valves V1–V7) in a predetermined way. In the illustrated and preferred embodiment, the applications reside as process software in EPROM's in the MPU 44.

An instrument manager 50 also resides as process software in EPROM's in the MPU 44. The instrument manager 50 communicates with the application control manager 46. The instrument manager 50 also communicates with low level peripheral controllers 52 for the pumps, solenoids, valves, and other functional hardware of the system.

Figure 2:
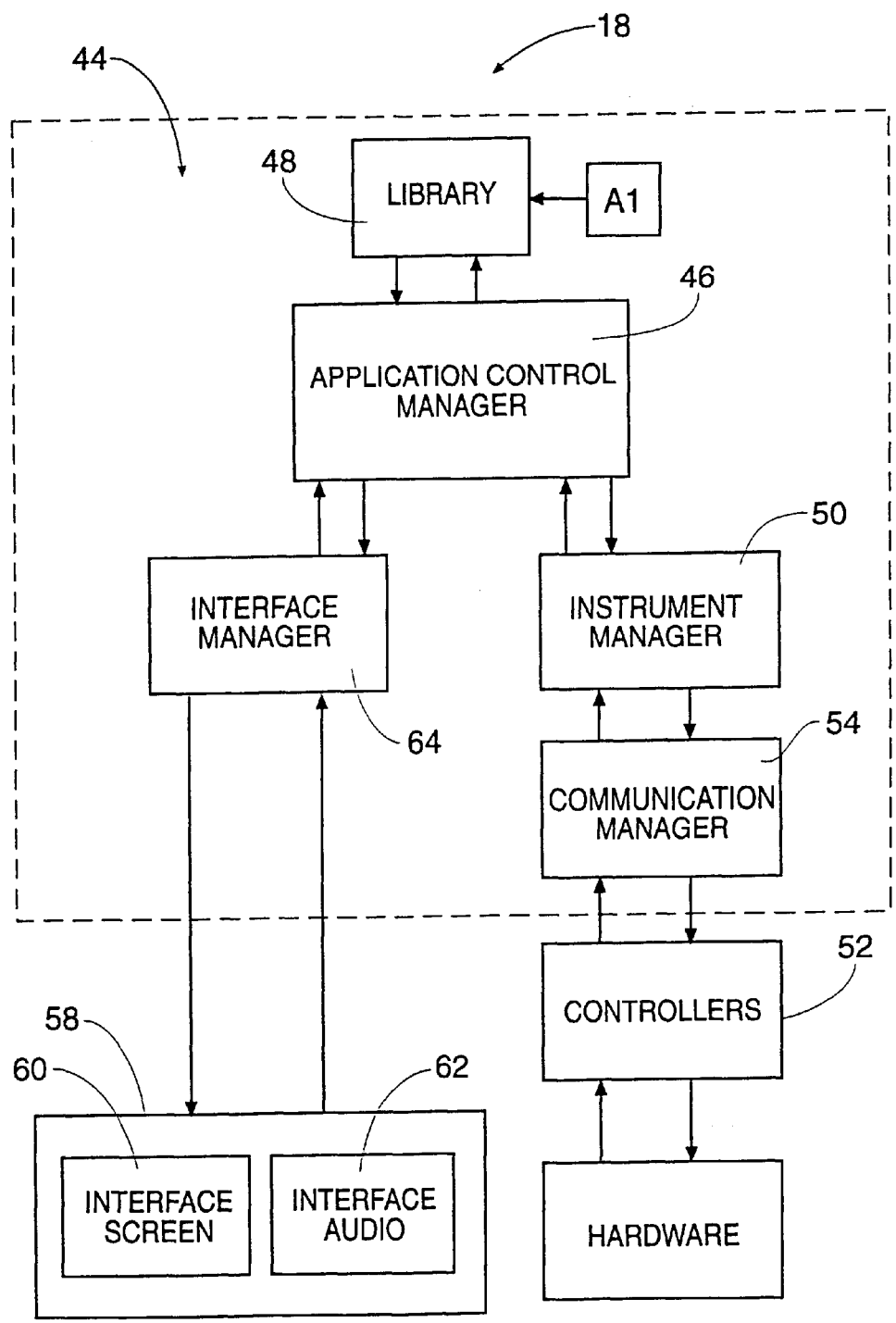
FIG. 2 is a schematic view of a controller that governs the operation of the blood processing system shown in FIG. 1.

As FIG. 2 shows, the application control manager 46 sends specified function commands to the instrument manager 50, as called up by the activated application. The instrument manager 50 identifies the peripheral controller or controllers 52 for performing the function and compiles hardware-specific commands. The peripheral controllers 52 communicate directly with the hardware to implement the hardware-specific commands, causing the hardware to operate in a specified way. A communication manager 54 manages low-level protocol and communications between the instrument manager 50 and the peripheral controllers 52.

As FIG. 2 also shows, the instrument manager 50 also conveys back to the application control manager 46 status data about the operational and functional conditions of the processing procedure. The status data is expressed in terms of, for example, fluid flow rates, sensed pressures, and fluid volumes measured.

The application control manager 46 transmits selected status data for display to the operator. The application control manager 46 transmits operational and functional conditions to the procedure application A1 and the performance monitoring application A2.

B. Operator Interface

In the illustrated embodiment, the MPU 44 also includes an interactive user interface 58. The interface 58 allows the operator to view and comprehend information regarding the operation of the system 10. The interface 58 also allows the operator to select applications residing in the application control manager 46, as well as to change certain functions and performance criteria of the system 10.

The interface 58 includes an interface screen 60 and, preferably, an audio device 62. The interface screen 60 displays information for viewing by the operator in alpha-numeric format and as graphical images. The audio device 62 provides audible prompts either to gain the operator's attention or to acknowledge operator actions.

In the illustrated and preferred embodiment, the interface screen 60 also serves as an input device. It receives input from the operator by conventional touch activation. Alternatively or in combination with touch activation, a mouse or keyboard could be used as input devices.

An interface manager 64 communicates with the interface screen 60 and audio device 62. The interface manager 64, in turn, communicates with the application control manager 46. The interface manager 64 resides as process software in EPROM's in the MPU 44.

Further details of the MPU 44 and interface 58 are disclosed in Lyle et al. U.S. Pat. No. 5,581,687, which is incorporated herein by reference.

C. System Control Functions

In the illustrated embodiment (as FIG. 2 shows), the library 48 includes at least one system control application A1. The system control application A1 contains several specialized, yet interrelated utility functions. Of course, the number and type of utility functions can vary.

In the illustrated embodiment, a utility function Fl derives the platelet yield (Yld) of the system 10. The utility function Fl ascertains both the instantaneous physical condition of the system 10 in terms of its separation efficiencies and the instantaneous physiological condition of the donor in terms of the number of circulating platelets available for collection. From these, the utility function F1 derive the instantaneous yield of platelets continuously over the processing period.

Another utility function F2 relies upon the calculated platelet yield (Yld) and other processing conditions to generate selected informational status values and parameters. These values and parameters are displayed on the interface 58 to aid the operator in establishing and maintaining optimal performance conditions. The status values and parameters derived by the utility function F2 can vary. For example, in the illustrated embodiment, the utility function F2 reports remaining volumes to be processed, remaining processing times, and the component collection volumes and rates.

Other utility functions generate control variables based upon ongoing processing conditions for use by the applications control manager 46 to establish and maintain optimal processing conditions. For example, one utility function F3 generates control variables to optimize platelet separation conditions in the first stage 24. Another utility function F4 generates control variables to control the rate at which citrate anticoagulant is returned with the PPP to the donor to avoid potential citrate toxicity reactions.

Further details of these and other utility functions can be found in Brown U.S. Pat. No. 5,676,841, which is incorporated herein by reference. A summary of various utility functions relied upon is found at the end of the Specification.

III. System Operation

In the illustrated embodiment, the system 10 is conditioned to achieve at least three processing objectives. The first objective is the collection of a desired yield of concentrated platelets (PC). The second objective is the collection of a desired volume of PPP to serve as a storage medium for the collected PC. The third objective is the collection of a desired volume of red blood cells (RBC) Other objectives may be established, e.g., to collect an additional volume of PPP for storage.

To achieve these objectives, the utility function Fl conditions the system 10 to collect and process blood in at least three different operating modes.

In the first operating mode, the system 10 is conditioned to process whole blood and collect PC and PPP. In the first mode, RBC are not concurrently collected, but are returned to the donor. PPP in excess of that desired may also be returned to the donor.

In the second operating mode, the system 10 is conditioned to process whole blood and concurrently collect RBC along with the associated additional volumes of PC and PPP. During the second mode, no blood components are returned to the donor.

In the third operating mode, the system 10 is conditioned to perform a final blood volume trimming function. During the volume trimming function, a portion of the collected RBC volume, or all or some of the collected PPP volume, or both, can be returned to the donor. The volume trimming function assures that component volumes actually collected do not exceed the volumes targeted for collection.

At the outset of the processing procedure, the operator uses the interface 58 to input the desired PC yield to be collected ($Yld_{Goal}$), the desired RBC volume to be collected ($RBC_{Goal}$), and the desired PPP volume to be collected ($PPP_{Goal}$).

The controller 18 conditions the system 10 to proceed with blood processing in the first operating mode. The controller 18 takes into account two processing variables in commanding a change from the first operating mode to the second operating mode, and from the second operating mode to the third operating mode. The first processing variable is the remaining whole blood volume needed to achieve the desired platelet yield, or $Vb_{rem}$ (in ml). The second processing variable is the volume of whole blood that is needed to be processed to achieve the desired volume of red blood cells $RBC_{Goal}$, or $Vb_{RBC}$.

When $Vb_{rem}=Vb_{RBC}$, the controller 18 switches from the first operating mode to the second operating mode. When $Vb_{rem}$ becomes zero, the controller switches from the second operating mode to the third operating mode.

A. Calculating $Vb_{rem}$

The utility function F2 relies upon the calculation of Yld by the first utility function F1 to derive the whole blood volume needed to be processed to achieve $Yld_{Goal}$. During blood processing, the utility function F2 continuously derives the additional processed volume needed to achieve the desired platelet yield $Vb_{rem}$ (in ml) by dividing the remaining yield to be collected by the expected average platelet count over the remainder of the procedure, with corrections to reflect the current operating efficiency $\eta_{Plt}$.

In the illustrated embodiment, the utility function F2 derives this value using the following expression:

$$Vb_{rem} = \frac{200{,}000 \times (Yld_{Goal} - Yld_{Current})}{\eta_{Plt} \times ACDil \times (Plt_{Current} + Plt_{Post})}$$

where:

$Yld_{Goal}$ is the desired platelet yield (k/µl), $Vb_{rem}$ is the additional processing volume (ml) needed to achieve $Yld_{Goal}$.

$Yld_{Current}$ is the current platelet yield (k/µl) calculated by the utility function F1 based upon current processing values (as set forth in the Summary that follows).

$\eta_{Plt}$ is the present (instantaneous) platelet collection efficiency, which can be calculated based upon current processing values (as set forth in the Summary that follows).

ACDil is an anticoagulant dilution factor (as set forth in the Summary that follows).

$Plt_{current}$ is the current (instantaneous) circulating donor platelet count, calculated based upon current processing values (as set forth in the Summary that follows).

$Plt_{Post}$ is the expected donor platelet count after processing, also calculated based upon total processing values (as set forth in the Summary that follows).

B. Calculating $Vb_{RBC}$

The utility function F2 derives $Vb_{RBC}$ based upon $RBC_{Goal}$, and also by taking into account the donor's whole blood hematocrit (Hct). The donor's whole blood hematocrit Hct can comprise a value measured at the outset of the procedure, or a value that is sensed on-line during the course of the procedure.

In the illustrated embodiment, Hct is not directly measured or sensed. Instead, the controller 18 relies upon an apparent hematocrit value $H_b$ of whole blood entering the separation chamber. $H_b$ is derived by the controller 18 based upon sensed flow conditions and theoretical consideration. The derivation of $H_b$ is described in more detail in the Summary that follows.

Based upon $H_b$, the utility function F2 can derive $Vb_{RBC}$ using the following expression:

$$Vb_{RBC} = \frac{RBC_{Goal} + Buf}{H_b}$$

where:

Buf is a prescribed buffer volume, e.g., 20 ml.

In the illustrated embodiment, the utility function F2 provides a further volume buffer, by rounding up the calculated volume of $Vb_{RBC}$, e.g., to the next highest integer divisible by ten.

In the illustrated embodiment, the utility function F2 also compares the calculated value of $Vb_{RBC}$ to a prescribed maximum volume (e.g., 600 mL). If $Vb_{RBC}$ equals or exceeds the prescribed maximum, the utility function F2 rounds the value down to a prescribed lesser amount, e.g., to 595 mL.

C. The First Operating Mode

In the first or non-concurrent operating mode, the system 10 processes whole blood and collects PC and PPP for storage. During the first mode, RBC and the uncollected volume of PPP are returned to the donor.

The system 10 shown in FIG. 1 employs one, single lumen phlebotomy needle 22. During the non-concurrent mode, the controller 18 operates the system 10 in successive draw and return cycles. During the draw cycle (FIG. 3), the controller 18 supplies the donor's WB through the needle 22 to the chamber 16 for processing. During the return cycle (FIG. 4), the controller 18 returns the RBC and PPP blood components to the donor through the same needle 22.

In the illustrated embodiment, the system 10 is configured to enable separation to occur in the chamber 16 without interruption during a succession of draw and return cycles. More particularly, the system 10 includes a draw reservoir 66. During a draw cycle (FIG. 3), a quantity of the donor's WB is pooled in the reservoir 66, in excess of the volume which is sent to the chamber 16 for processing. The system 10 also includes a return reservoir 68. A quantity of RBC collects in the return reservoir 68 during the draw cycle for periodic return to the donor during the return cycle (see FIG. 4). During the return cycle, WB is conveyed from the draw reservoir 66 to the chamber 16 to sustain uninterrupted separation.

Figure 3:
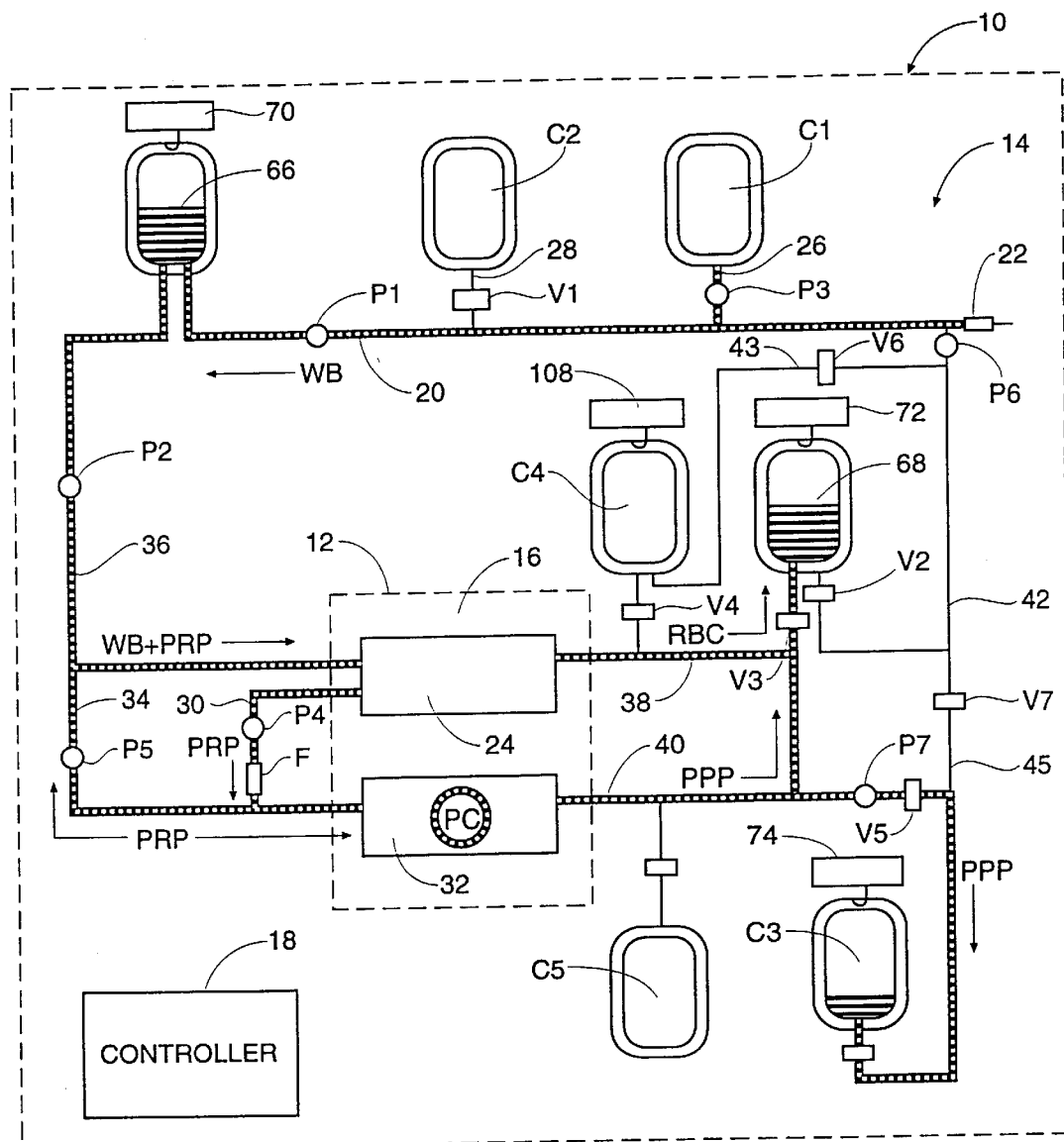
FIG. 3 is a diagrammatic view of the blood processing system shown in FIG. 1 conditioned by the controller to perform a draw cycle during a non-concurrent collection mode.
Figure 4:
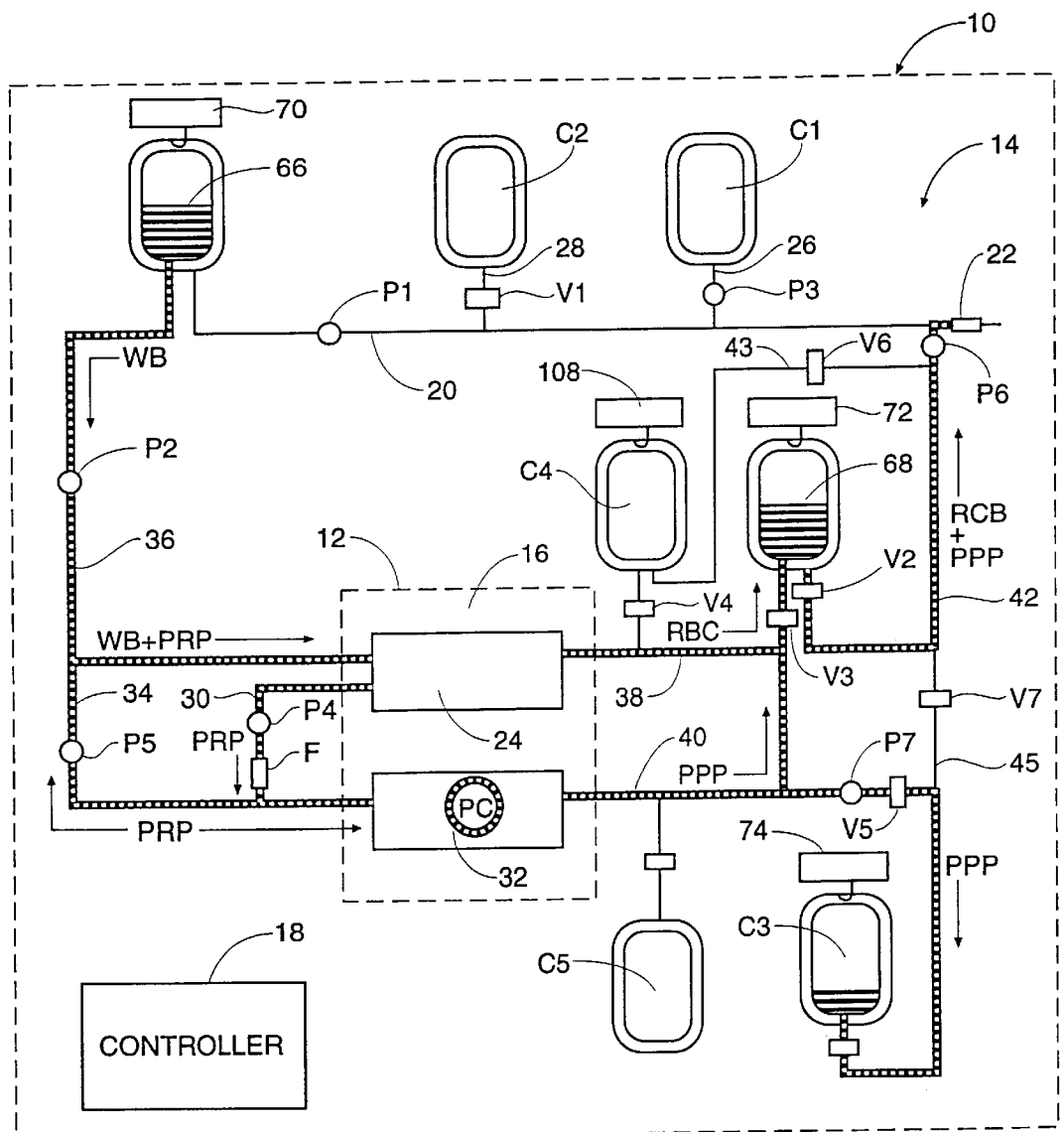
FIG. 4 is a diagrammatic view of the blood processing system shown in FIG. 1 conditioned by the controller to perform a return cycle during a non-concurrent collection mode.

In a draw cycle of the non-concurrent mode FIG. 3), the whole blood pump P1 direct WB from the needle 22 through a first tubing branch 20 and into the draw reservoir 66. Meanwhile, an auxiliary tubing branch 26 meters anticoagulant from the container C1 to the WB flow through the anticoagulant pump P3. While the type of anticoagulant can vary, the illustrated embodiment uses ACDA, which is a commonly used anticoagulant for pheresis.

A container C2 holds saline solution. Another auxiliary tubing branch 28 conveys the saline into the first tubing branch 20, via the in line valve V1, for use in priming and purging air from the assembly 14 before processing begins. Saline solution is also introduced again after processing ends to flush residual components from the assembly 14 for return to the donor.

The processing controller 18 receives processing information from a weigh scale 70. The weigh scale 70 monitors the volume of WB collected in the draw reservoir 66. Once the weigh scale 70 indicates that a desired volume of WB is present in the draw reservoir 66, the controller 18 commands the whole blood processing pump P2 to operate to continuously convey WB from the draw reservoir 66 into the first stage 24 of the processing chamber 16 through inlet branch 36. The controller 18 operates the whole blood pump P1 at a higher flow rate (at, for example, 100 ml/min) than the whole blood processing pump P2, which operates continuously (at, for example, 50 ml/min), so a volume of anticoagulated blood collects in the reservoir 66. By monitoring weight using the weigh scale 70, the controller intermittently operates the whole blood inlet pump Pi to maintain a desired volume of WB in the draw reservoir 66.

Anticoagulated WB enters and fills the first stage 24 of the processing chamber 16. There, centrifugal forces generated during rotation of the centrifuge 12 separate WB into red blood cells (RBC) and platelet-rich plasma (PRP).

A PRP pump P4 operates to draw PRP from the first stage 24 of the processing chamber 16 into a second tubing branch 30 for transport to the second stage 32 of the processing chamber 16. There, the PRP is separated into platelet concentrate (PC) and platelet-poor plasma (PPP).

The controller 18 optically monitors the location of the interface between RBC and PRP within the first stage 24 of the processing chamber 16. The controller 18 operates the PRP pump P4 to keep the interface at a desired location within the first stage 24 of the processing chamber 24. This keeps a substantial portion of the leukocytes, which occupy the interface, from entering the flow of PRP.

Optionally, the PRP can also be conveyed through a filter F to remove leukocytes before separation in the second stage 32. The filter F can employ filter media containing fibers of the type disclosed in Nishimura et al U.S. Pat. No. 4,936, 998, which is incorporated herein by reference. Filter media containing these fibers are commercially sold by Asahi Medical Company in filters under the trade name SEPA-CELL.

The system 10 includes a recirculation tubing branch 34 and an associated recirculation pump P5. The processing controller 18 operates the pump P5 to divert a portion of the PRP exiting the first stage 24 of the processing chamber 16 for remixing with the WB entering the first stage 24 of the processing chamber 16. The recirculation of PRP establishes desired conditions in the entry region of the first stage 24 to provide maximal separation of RBC and PRP.

A RBC branch 38 conveys the RBC from the first stage 24 of the processing chamber 16 to the return reservoir 68 (which is controlled by valve V3). A weigh scale 72 monitors the volume of PPP collected in the container C4.

A PPP branch 40 conveys PPP from the second stage 32 of the processing chamber 16, by operation of the PPP pump P7. By opening valve V5, all or a portion of the PPP can be directed to a collection container C4, depending upon the flow rate of the pump P7. A weigh scale 74 monitors the volume of PPP collected in the container C4. The PPP that is not collected flow into the return reservoir 68, where it mixes with the RBC.

During the second operating mode (which will be described later), a relatively large volume of PPP (i.e., from about 50% to 75% of $PPP_{Goal}$) will typically be collected without return to the donor. In anticipation of this, the controller 16 limits the rate at which PPP is collected during the first mode. This avoids the collection of a surplus volume of PPP at the end of the procedure. By limiting the rate at which PPP is collected during the first operating mode, the controller 18 reduces the time of the subsequent blood volume trimming function, thereby reducing the overall procedure time. The small volume of surplus PPP also allows the use of higher return flow rates during the blood volume trimming function, as the amount of anticoagulant (carried in the PPP) that is returned to the donor during the blood volume trimming function is reduced.

The controller 18 receives processing information from the weigh scale 72, monitors the volume of RBC and PPP in the return reservoir 68. When a preselected volume exists, the controller 18 shifts the operation of the system 10 from a draw cycle to a return cycle.

In the return cycle (FIG. 4), the controller 18 stops the whole blood inlet pump P1 and anticoagulant pump P3 and starts a blood return pump P6. A return branch 42 conveys RBC and PPP in the return reservoir 68 to the donor through the needle 22.

Meanwhile, while in the return cycle, the controller 18 keeps the WB processing pump P2, the PRP pump P4, and recirculation pump P5 in operation to continuously process the WB pooled in the draw reservoir 66 through the first stage and second stages 24 and 32 of the chamber 16.

When the weigh scale 72 indicates that the contents of the return reservoir 68 have been conveyed to the donor, the controller 18 shifts operation of the system 10 to another draw cycle.

The controller 18 toggles between successive draw and return cycles until $Vb_{rem}=Vb_{RBC}$. When $Vb_{rem}=Vb_{RBC}$, the controller 18 commands a final return cycle, to return the contents of the return reservoir 68 to the donor. Upon returning the contents of the return reservoir 68, the controller 18 switches from the first operating mode to the second operating mode.

D. Concurrent Collection Mode

Figure 5:
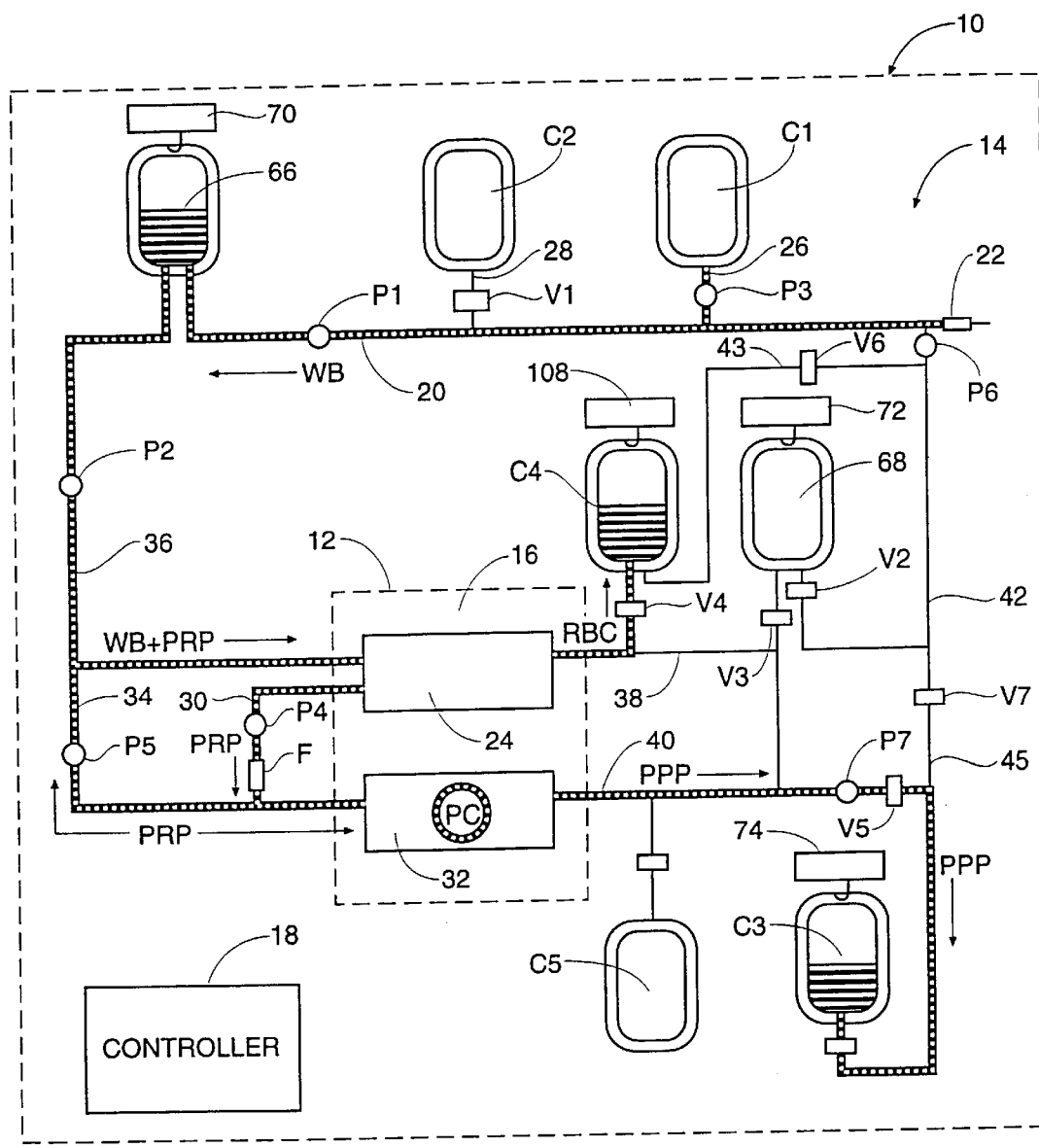
FIG. 5 is a diagrammatic view of the blood processing system shown in FIG. 1 conditioned by the controller to perform a concurrent collection mode.

In a second or concurrent collection mode (FIG. 5), the controller 18 conditions to system 10 to operate in a sustained draw cycle, to process whole blood and concurrently collect the targeted volume of RBC, along with associated additional volumes of PC and PPP. During the concurrent collection mode, the controller 18 does not switch operation of the system 10 to a return cycle. There is only one sustained draw cycle during the concurrent collection mode, and no components are returned to the donor.

During the sustained draw cycle of concurrent collection mode, the controller 18 avoids the collection of a large surplus volume of whole blood in the draw reservoir 66. In the illustrated embodiment, the controller 18 achieves this objective by maintaining a smaller flow rate differential between the whole blood inlet pump P1 and the whole blood processing pump P2, compared to the differential maintained during the draw cycle of non-concurrent collection mode. For example, in the illustrated embodiment, the whole blood inlet pump Pi is operated at a minimal differential of, e.g., only 1 mL/min, above the whole blood processing pump P2.

To further assure that only a slight buffer volume of whole blood is maintained in the draw reservoir 66 during the sustained draw cycle of concurrent collection mode, the weight scale 70 toggles the whole blood inlet pump Pi and anticoagulant pump P3 off whenever the sensed volume of blood in the draw reservoir 66 exceeds a specified minimum buffer amount, e.g., 5 g.

During the sustained draw cycle of concurrent collection mode, red blood cells are directed into a collection container C4, via the valve V4, which is opened for this purpose (return valve V3 is closed, so no RBC collect in the return reservoir 68). A weigh scale 108 monitors the weight of the collection container C4.

An associated volume of PC collects in the second stage 32 of the chamber 16, while the associated volume of PPP collects in the collection container C3 (through the operation of the PPP pump P7 and valve V5, which is opened). Valve V3 is closed, so no PPP collects in the return reservoir 68.

The controller 18 continuously derives $Vb_{rem}$ during the sustained draw cycle of concurrent collection mode. When $Vb_{rem}$ becomes zero, the controller 18 terminates the concurrent collection mode.

E. Blood Volume Trimming Function

Figure 6:
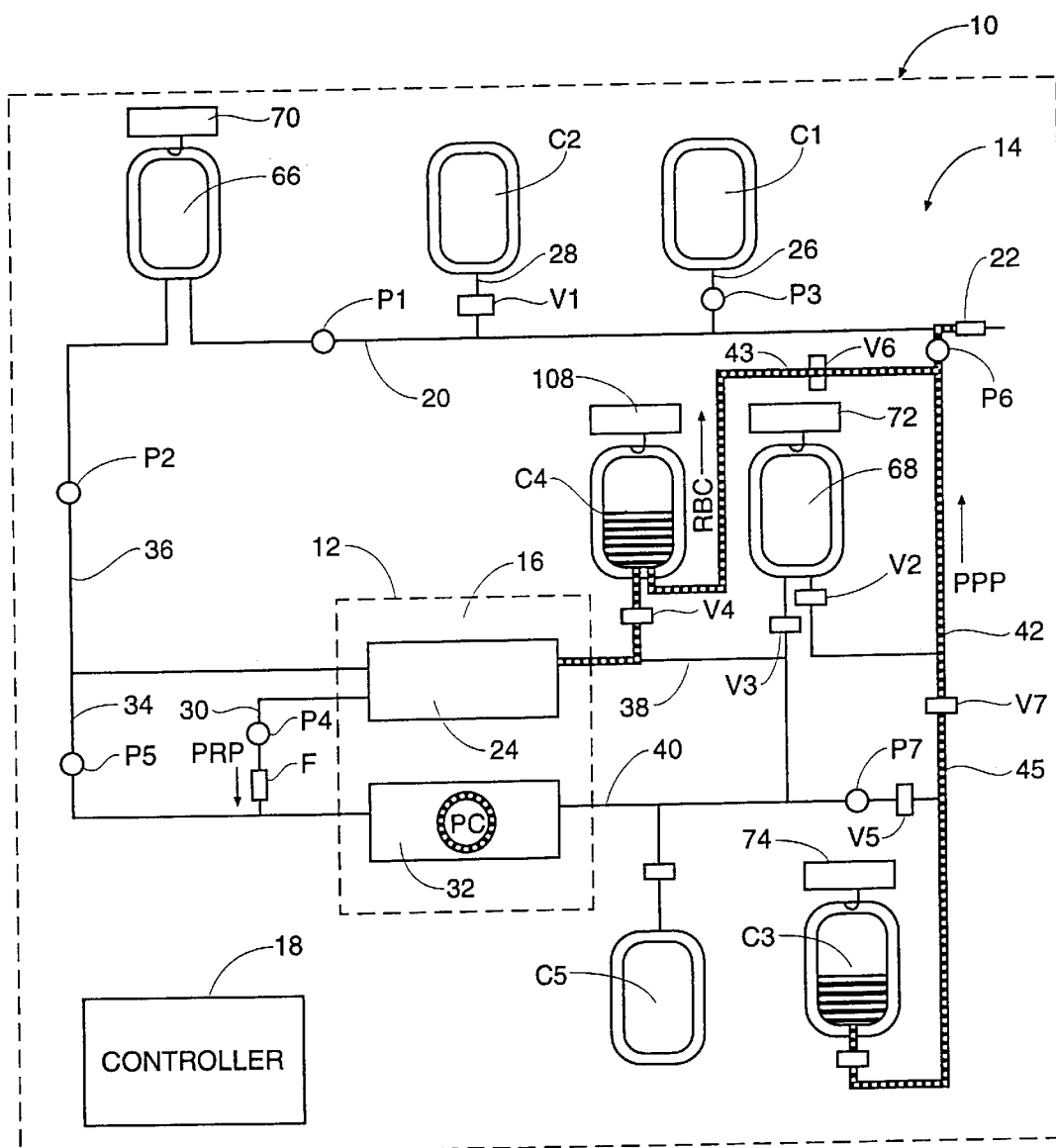
FIG. 6 is a diagrammatic view of the blood processing system shown in FIG. 1 conditioned by the controller to perform a blood volume trimming function.

In the illustrated embodiment (see FIG. 6), at the end of the concurrent collection mode, the controller 18 assesses the volumes of RBC and PPP that have been collected, using weigh scales 108 and 74, respectively.

If the volume of RBC collected exceeds $RBC_{Goal}$, the controller 18 commands the system 10 to enter a return cycle to return the excess RBC volume to the donor from the collection container C4, through the branch path 43 (valve V6 being opened), and into the return path 42 (valve V2 being closed), by operation of the in-line return pump P6.

Likewise, if the volume of PPP collected exceeds $PPP_{Goal}$, the controller 18 commands the system 10 to enter a return cycle to return the excess PPP volume to the donor from the collection container C3, through the branch path 45 (valve V7 being opened and valve V5 being closed), and into the return path 42, by operation of the in-line return pump P6.

At the end of the blood volume trimming function, the controller 18 commands a saline reinfusion operation to return residual blood in the system 10 to the donor, along with a prescribed fluid replacement volume.

F. Post Collection Processing

1. PPP

The retention of PPP can serve multiple purposes, both during and after the component separation process.

The retention of PPP serves a therapeutic purpose during processing. PPP contains most of the anticoagulant that is metered into WB during the component separation process. By retaining a portion of PPP instead of returning it all to the donor, the overall volume of anticoagulant received by the donor during processing is reduced. This reduction is particularly significant when large blood volumes are processed. The retention of PPP during processing also keeps the donor's circulating platelet count higher and more uniform during processing.

The system 10 can also derive processing benefits from the retained PPP. For example, the system 10 can, in an alternative recirculation mode, recirculate a portion of the retained PPP, instead of PRP, for mixing with WB entering the first compartment 24. Or, should WB flow be temporarily halted during processing, the system 10 can draw upon the retained volume of PPP as an anticoagulated "keep-open" fluid to keep fluid lines patent. In addition, at the end of the separation process, the system 10 can draw upon the retained volume of PPP as a "rinse-back" fluid, to resuspend and purge RBC from the first stage compartment 24 for return to the donor through the return branch 42.

2. PC

After the separation process, the system 10 also operates in a resuspension mode to draw upon a portion of the retained PPP to resuspend PC in the second stage 24 for transfer and storage in the collection container(s) C5. Resuspension and transfer of PC to the collection containers C5 can be accomplished manually or on line.

Preferable, the container(s) C5 intended to store the PC are made of materials that, when compared to DEHP-plasticized polyvinyl chloride materials, have greater gas permeability that is beneficial for platelet storage. For example, polyolefin material (as disclosed in Gajewski et al U.S. Pat. No. 4,140,162), or a polyvinyl chloride material plasticized with tri-2-ethylhexyl trimellitate (TEHTM) can be used.

G. RBC

Figure 7:
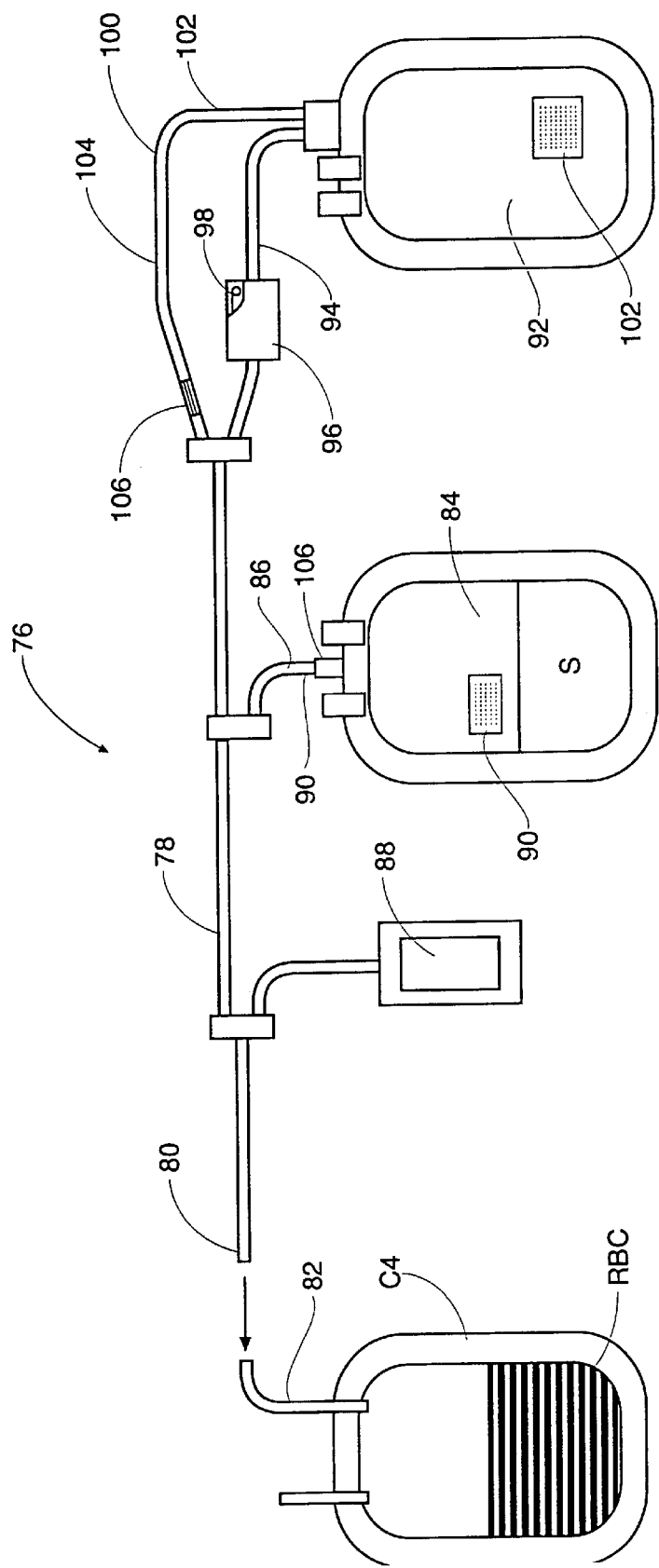
FIG. 7 is a front view of a blood collection set, which, in use, receives red blood cells after collection in the system shown in FIG. 1 for further processing prior to storage.

In the illustrated embodiment (see FIG. 7), a disposable collection set 76 is provided to process the RBC volume collected for storage.

The set 76 includes a transfer path 78. The transfer path 78 has a sealed free end 80 designed to be connected in a sterile fashion to a sealed tube segment 82 on the RBC collection container C4 (see FIG. 7). Known sterile connection mechanisms (not shown) like that shown in Spencer U.S. Pat. No. 4,412,835 can be used for connecting the transfer path 78 to the tube segment 82. These mechanisms form a molten seal between tubing ends, which, once cooled, forms a sterile weld.

A first bag 84 communicates with the transfer path 78 through a length of sample tubing 86. The first bag 84 contains a red blood cell additive solution S, e.g., SAG-M or ADSOL® Solution (Baxter Healthcare Corporation). Following coupling of the collection set 76 to the RBC collection container C4, a conventional in-line frangible cannula 106 in the sample tubing 86 is opened, and the red blood cell additive solution S is transferred from the first bag 84 into the collection container C4 for mixing with the collected RBC volume. The mixture of additive solution and RBC can then be transferred back into the first bag 84.

Residual air in the first bag 84 can be vented into an in-line air venting chamber 88, which communicates with the transfer path 78. At the same time, an aliquot of the collected RBC volume present in the first bag 84 can be expressed into the sample tubing 86.

The tubing 86 preferably carries an identification code 90 which is identical to a code 90 printed on or otherwise applied to the first bag 84. The tubing 86 is then closed with a conventional snap-apart seal, and the first bag 84 is detached from the collection set 76 for storing the RBC volume. The tubing 86 can be further sealed in segments, using conventional tube sealers, to isolate multiple samples of the RBC for analysis and cross-matching.

The set 76 also includes a second bag 92, which communicates with the transfer path 78 downstream of the first bag 84 through a branch path 94. The branch path 94 includes an in-line filter 96. The in-line filter 96 carries a filtration medium 98 that selectively removes leukocytes from red blood cells. The filter can comprise, e.g., a R-3000 Red Blood Cell Filter (Asahi Medical).

The mixture of red blood cells and additive solution can be transferred from the collection bag C4 to the second bag 92 through the in-line filter 96, by-passing the first bag 84. In this way, the set 76 provides red blood cells essentially free of leukocytes, suitable for long term storage.

An air venting path 100 extends from the second bag 92 to the transfer path 78, bypassing the in-line filter 96. By opening a conventional break-away cannula 106 in the path 100, residual air in the second bag 92 can be vented through the path 100 into the in-line air venting chamber 88. A one-way valve 104 in the path 100 allows air and liquid flow in the path 100 away from the bag 92, but not in the opposite direction.

At the same time, an aliquot of the collected RBC present in the second bag 92 can be expressed into the venting path 100. The venting path 100 carries an identification code 102 which is identical to a code 102 printed on or otherwise applied to the second bag 92. The venting path 100 and branch path 94 can be closed with a conventional snap-apart seal, to allow detachment of the second bag 92 from the transfer path 78. The path 100 can also be sealed in segments, to provide multiple samples of the RBC for analysis and cross-matching.

The collection set 76 provides the flexibility to provide a red blood cell product suitable for long term storage, which is either non-leukocyte reduced or leukocyte reduced before storage.

IV. Estimating Post-procedure Donor Blood Status

In addition to the information that the utility functions F1 to F4 provide before, during, and after a selected blood processing procedure, the controller 18 can also include utility functions F5 and F6, which provide additional information before, during, or after the procedure, estimating the effect of the selected procedure upon the donor's blood volume and hematocrit. More particularly, additional utility function F5 provides an estimation of the donor's net fluid volume deficit as a result of the procedure, which will be called the Post-Intravascular Volume Deficit or Post-IVD. The additional utility function F6 provides an estimation of the hematocrit of the donor's blood after the procedure, which will be called the Post-Hematocrit. The utility functions F5 and F6 can be performed after any selected blood processing procedure, e.g., after a procedure that collects platelets without collecting red blood cells, or after a procedure that collects both platelets and red blood cells.

Post-IVD or Post-Hematocrit can be derived by the utility functions F5 or F6 at the beginning of the selected procedure based upon the operating parameters existing at that time. Post-IVD or Post-Hematocrit can be updated by the utility functions F5 or F6 at any time during the selected procedure as operating parameters change or are changed by the operator.

The controller 18 desirably displays the values of the Post-Intravascular Volume Deficit, or other expressions thereof, and the Post-Hematocrit on the interface 58. The information can also be presented in printed form, e.g., for paper record filing, or in data form for offloading, e.g., to a centralized donor database.

Access to this information before, during, or after the selected procedure aids the operator in assessing the effect of the procedure on the donor's blood volume. This information allows a blood center to assess the effect of a given procedure upon the donor, so that a blood center can optimize its collection of blood products from a donor, without compromising donor safety or regulatory requirements.

A. Utility Function F5: Deriving Post-intravascular Volume Deficit

The Post-Intravascular Volume Deficit (Post-IVD) is defined as the total maximum blood volume that the intended procedure will remove from the donor, minus replacement volume of fluids (TotVolReplaced) provided to the donor over the course of the procedure. Stated differently, the Post-Intravascular Volume Deficit (Post-IVD) is an assessment of the donor's net fluid volume deficit resulting from the procedure.

To derive the Post-Intravascular Volume Deficit Post-IVD), the utility function F5 derives the donor's total blood volume (DonVol) at the start of the procedure. DonVol is based upon the donor's gender, height, and weight. DonVol can be derived empirically, e.g., according to Equation (13) in the Summary below.

The utility function F5 also derives the total volume of blood products to be removed from the donor during the procedure. This comprises the sum of the desired PC yield to be collected ($Yld_{Goal}$), the desired RBC volume to be collected ($RBC_{Goal}$), and the desired PPP volume to be collected ($PPP_{Goal}$). Of course, depending upon objectives of the particular selected procedure, one or more of these blood volumes may be zero, if that blood product is not targeted for collection by the procedure. These targeted values are inputted by the operator at the beginning of a given procedure, and can be modified by the operator during the course of the procedure.

The utility function F5 also desirably accounts for other blood losses the donor will experience, due to, e.g., the residual red blood cell volume of the blood processing system, any cycle volume (for single needle systems), or any other blood volumes (Res-Vol) that will not be returned to the donor at the end of the procedure. In this respect, the utility function F5 conducts a "worst case" blood loss scenario, one that goes beyond accounting for only the volume of blood products collected, and one that also accounts for blood loss from other sources, to assess an actual total blood volume loss from all sources.

The sum of the blood product volumes and Res-Vol comprise the total blood volume loss that the donor will experience as a result of the procedure (TotVolRemoved), expressed as follows:

$$TotVolRemoved=(Yld_{Goal})+(RBC_{Goal})+(PPP_{Goal})+(Res\text{-}Vol)$$

The utility function F5 also derives the total volume of replacement fluid (TotVolReplaced) that will be returned to the donor during the procedure. This includes the volume of saline given to the donor at the beginning of the procedure due to saline prime, plus the estimated volume of anticoagulant ACD to be used during the procedure. The sum of these volumes comprise the total replacement fluid volume for the procedure (TotVolReplaced).

To derive Post-Intravascular Volume Deficit (Post-IVD), the utility function F5 subtracts TotVolReplaced from TotVolRemoved, expressed as follows:

$$Post\text{-}IVD=TotVolRemoved-TotVolReplaced$$

Numeric information pertaining to Post-IVD is desirably expressed to the operator in one or more different formats, which relay the information in the context of, e.g., a blood center policy or a regulatory requirement. For example, Post Procedure Net Fluid Deficit Information can express Post-IVD as the percentage of the donor's total blood volume prior to the procedure (DonVol), that is:

$$Post\text{ }Procedure\text{ }Net\text{ }Fluid\text{ }Deficit\text{ }Information(\%)=Post\text{-}IVD/DonVol.$$

As another example, Post Procedure Net Fluid Deficit Information can express Post-IVD as a fraction of the donor's weight (Wgt) (in kg), that is:

$$Post\text{ }Procedure\text{ }Net\text{ }Fluid\text{ }Deficit\text{ }Information\text{ }(mL/kg)=Post\text{-}IVD/Wgt.$$

The controller 18 can include programming that compares Post-IVD or Post Procedure Net Fluid Deficit Information to prescribe standards. The controller 18 can produce a cautionary output based upon the comparison, if the derived value is not consistent with the prescribed standards.

B. Utility Function F6: Deriving Post-hematocrit

The Post-Hematocrit is defined as an estimation of the donor's total red blood cell volume remaining after the intended procedure divided by an estimation of the donor's total blood fluid volume remaining after the intended procedure.

In deriving Post-Hematocrit, the utility function F6 relies upon three estimated quantities: (i) the donor's red blood cell volume existing prior to the procedure (Pre-RBC-Vol), which is a function of the donor's blood hematocrit measured prior to the procedure (Pre-Hct); (ii) the donor's red blood cell volume remaining after the procedure (Post-RBC-Vol), which is a function of the desired RBC volume to be collected ($RBC_{Goal}$) and system residual red blood cell volume (Res-Vol)(also used by utility function F5 above); and (iii) the donor's total blood volume after the procedure (Post-Tot-Vol), which is a function of donor's total blood volume existing prior to the procedure (DonVol) and the Post-Intravascular Volume Deficit (Post-IVD), as derived by utility function F5.

More particularly, to estimate Pre-RBC-Vol, an actual measurement of the donor's blood hematocrit (Pre-Hct) before the procedure is preferably relied upon. The value of Pre-Hct is inputted to the controller 18 for processing by the utility function F6. Alternatively, an accurate estimation of the donor's blood hematocrit before the procedure can be used as Pre-Hct. To derive Pre-RBC-Vol, the utility function F6 multiplies the donor's total blood volume (DonVol) prior to procedure (derived in the same manner as utility function F5) by the donor's blood hematocrit prior to the procedure (Pre-Hct), expressed as follows:

$$Pre\text{-}RBC\text{-}Vol=DonVol\times Pre\text{-}Hct$$

To estimate Post-RBC-Vol, the utility function F6 subtracts the sum of the desired RBC volume to be collected ($RBC_{Goal}$) and the system residual blood volume (Res-Vol) (also used by utility function F5 above) from the donor's pre-procedure red blood cell volume (Pre-RBC-Vol), expressed as follows:

$$Post\text{-}RBC\text{-}Vol=Pre\text{-}RBC\text{-}Vol-(RBC_{Goal}+Res\text{-}Vol)$$

To determine Post-Tot-Vol, the utility function F6 subtracts from the donor's total blood volume existing prior to the procedure (DonVol), the Post-Intravascular Volume Deficit (Post-IVD), as derived by utility function F5, expressed as follows:

$$Post\text{-}Tot\text{-}Vol=DonVol-Post\text{-}IVD$$

To derive Post-Hematocrit, the utility function F6 divides the estimation of the donor's red blood cell volume existing after the procedure (Post-RBC-Vol) by the estimation of the donor's total blood volume existing after the procedure (Post-Tot-Vol), expressed as follows:

$$Post\text{-}Hematocrit=Post\text{-}RBC\text{-}Vol/Post\text{-}Tot\text{-}Vol$$

Information pertaining to Post-Hematocrit is desirably processed for display to the operator, along with the information pertaining to Post-IVD. Such information can also be presented in printed form or downloaded in electronic form for data storage and manipulation.

The controller 18 can include programming that compares Post-Hematocrit to prescribe standards. The controller 18 can produce a cautionary output based upon the comparison, if the derived value is not consistent with the prescribed standards.

V. Summary of the Other Processing Utility Functions F1 to F4

A. Deriving Platelet Yield

The utility function F1 makes continuous calculations of the platelet separation efficiency ($\eta_{Plt}$) of the system 10. The utility function F1 treats the platelet separation efficiency $\eta_{Plt}$ as being the same as the ratio of plasma volume separated from the donor's whole blood relative to the total plasma volume available in the whole blood. The utility function F1 thereby assumes that every platelet in the plasma volume separated from the donor's whole blood will be harvested.

The donor's hematocrit changes due to anticoagulant dilution and plasma depletion effects during processing, so the separation efficiency $\eta_{Plt}$ does not remain at a constant value, but changes throughout the procedure. The utility function F1 contends with these process-dependent changes by monitoring yields incrementally. These yields, called incremental cleared volumes ($\Delta ClrVol$), are calculated by multiplying the current separation efficiency $\eta_{Plt}$ by the current incremental volume of donor whole blood, diluted with anticoagulant, being processed, as follows:

$$\Delta ClrVol = ACDil \times \eta_{Plt} \times \Delta VOL_{Proc} \qquad \text{Eq (1)}$$

where:

$\Delta Vol_{Proc}$ is the incremental whole blood volume being processed, and

ACDil is an anticoagulant dilution factor for the incremental whole blood volume, computed as follows:

$$ACDil = \frac{AC}{AC+1} \qquad \text{Eq (2)}$$

where:

AC is the selected ratio of whole blood volume to anticoagulant volume (for example 10:1 or "10"). AC may comprise a fixed value during the processing period. Alternatively, AC may be varied in a staged fashion according to prescribed criteria during the processing period.

For example, AC can be set at the outset of processing at a lesser ratio for a set initial period of time, and then increased in steps after subsequent time periods; for example, AC can be set at 6:1 for the first minute of processing, then raised to 8:1 for the next 2.5 to 3 minutes; and finally raised to the processing level of 10:1.

The introduction of anticoagulant can also staged by monitoring the inlet pressure of PRP entering the second processing stage 32. For example, AC can be set at 6:1 until the initial pressure (e.g. at 500 mmHg) falls to a set threshold level (e.g., 200 mmHg to 300 mmHg). AC can then be raised in steps up to the processing level of 10:1, while monitoring the pressure to assure it remains at the desired level.

The utility function F1 also makes continuous estimates of the donor's current circulating platelet count ($Plt_{Circ}$), expressed in terms of 1000 platelets per microliter ($\mu l$) of plasma volume (or $k/\mu l$). Like $\eta_{Plt}$, $Plt_{Circ}$ will change during processing due to the effects of dilution and depletion. The utility function F1 incrementally monitors the platelet yield in increments, too, by multiplying each incremental cleared plasma volume $\Delta ClrVol$ (based upon an instantaneous calculation of $\eta_{Plt}$) by an instantaneous estimation of the circulating platelet count $Plt_{Clr}$. The product is an incremental platelet yield ($\Delta Yld$), typically expressed as $e^n$ platelets, where $e^n = 0.5 \times 10^n$ platelets ($e^{11} = 0.5 \times 10^{11}$ platelets).

At any given time, the sum of the incremental platelet yields $\Delta Yld$ constitutes the current platelet yield $Yld_{Current}$, which can also be expressed as follows:

$$Yld_{Current} = Yld_{Old} + \frac{\Delta ClrVol \times Plt_{Cur}}{100,000} \qquad \text{Eq (3)}$$

where: $Yld_{Old}$ is the last calculated $Yld_{Current}$, and $$\Delta Yld = \frac{\Delta ClrVol \times Plt_{Current}}{100,000} \qquad \text{Eq (4)}$$

where:

$Plt_{Current}$ is the current (instantaneous) estimate of the circulating platelet count of the donor.

$\Delta Yld$ is divided by 100,000 in Eq (4) to balance units.

The following provides further details in the derivation of the above-described processing variables by the utility function F1.

1. Deriving Overall Separation Efficiency $\eta_{Plt}$

The overall system efficiency $\eta_{Plt}$ is the product of the individual efficiencies of the parts of the system, as expressed as follows:

$$\eta_{plt} = \eta_{1stSep} \times \eta_{2ndSep} \times \eta_{Anc} \qquad \text{Eq (5)}$$

where:

$\eta_{1stSep}$ is the efficiency of the separation of PRP from WB in the first separation stage.

$\eta_{2ndSep}$ is the efficiency of separation PC from PRP in the second separation stage.

$\eta_{Anc}$ is the product of the efficiencies of other ancillary processing steps in the system.

a. First Stage Separation Efficiency $\eta_{1stSep}$

The utility function F1 derives $\eta_{1stSep}$ continuously over the course of a procedure based upon measured and empirical processing values, using the following expression:

$$\eta_{Sep} = \frac{Q_p}{(1 - H_b)Q_b} \qquad \text{Eq (6)}$$

where:

$Q_b$ is the measured whole blood flow rate (in ml/min)

$Q_p$ is the measured PRP flow rate (in ml/min).

$H_b$ is the apparent hematocrit of the anticoagulated whole blood entering the first stage separation compartment. $H_b$ is a value derived by the utility based upon sensed flow conditions and theoretical considerations. The utility function F1 therefore requires no on-line hematocrit sensor to measure actual WB hematocrit.

The utility function F1 derives $H_b$ based upon the following relationship:

$$H_b = \frac{H_{rbc}(Q_b - Q_p)}{Q_b} \qquad \text{Eq (7)}$$

where:

$H_{rbc}$ is the apparent hematocrit of the RBC bed within the first stage separation chamber, based upon sensed operating conditions and the physical dimensions of the first stage separation chamber. As with $H_b$, the utility function F1 requires no physical sensor to determine $H_{rbc}$, which is derived by the utility function according to the following expression:

$$H_{rbc} = 1 - \left(\frac{\beta}{gA\kappa S_\gamma}(q_b - q_p)\right)^{\frac{1}{k+1}} \quad \text{Eq (8)}$$

where:

$q_b$ is inlet blood flow rate (cm$^3$/sec), which is a known quantity which, when converted to ml/min, corresponds with $Q_b$ in Eq (6)

$q_p$ is measured PRP flow rate (in cm$^3$/sec), which is a known quantity which, when converted to ml/min corresponds with $Q_p$ in Eq (6)

β is a shear rate dependent term, and $S_\gamma$ is the red blood cell sedimentation coefficient (sec). Based upon empirical data, Eq (8) assumes that β/$S_\gamma$=5.8×10$^6$ sec$^{-1}$.

A is the area of the separation chamber (cm$^2$), which is a known dimension.

g is the centrifugal acceleration (cm/sec$^2$), which is the radius of the first separation chamber (a known dimension) multiplied by the rate of rotation squared Ω$^2$ (rad/sec$^2$) (another known quantity).

k is a viscosity constant=0.625, and κ is a viscosity constant based upon k and another viscosity constant α=4.5, where:

$$\kappa = \frac{k+2}{\alpha}\left[\frac{k+2}{k+1}\right]^{k+1} = 1.272 \quad \text{Eq (9)}$$

Eq (8) is derived from the relationships expressed in the following Eq (10):

$$H_{rbc}(1 - H_{rbc})^{(k+1)} = \frac{\beta H_b q_b}{qA\kappa S_\gamma} \quad \text{Eq (10)}$$

set forth in Brown, *The Physics of Continuous Flow Centrifugal Cell Separation*, "Artificial Organs" 1989; 13(1):4–20)). Eq (8) solves Eq (10) for $H_{rbc}$.

b. The Second Stage Separation Efficiency $\eta_{2ndSep}$

The utility function F1 also derives η2ndSepcontinuously over the course of a procedure based upon an algorithm, derived from computer modeling, that calculates what fraction of log-normally distributed platelets will be collected in the second separation stage 32 as a function of their size (mean platelet volume, or MPV), the flow rate ($Q_p$), area (A) of the separation stage 32, and centrifugal acceleration (g, which is the spin radius of the second stage multiplied by the rate of rotation squared Ω$^2$).

The algorithm can be expressed in terms of a function, which expressed $\eta_{2ndSep}$ in terms of a single dimensionless parameter $gAS_p/Q_p$, where:

$S_p$=1.8×10$^{-9}$ MPV$^{2/3}$ (sec), and

MPV is the mean platelet volume (femtoliters, fl, or cubic microns), which can be measured by conventional techniques from a sample of the donor's blood collected before processing. There can be variations in MPV due to use of different counters. The utility function therefore may include a look up table to standardize MPV for use by the function according to the type of counter used. Alternatively, MPV can be estimated based upon a function derived from statistical evaluation of clinical platelet precount $Plt_{PRE}$ data, which the utility function can use. The inventor believes, based upon his evaluation of such clinical data, that the MPV function can be expressed as:

$$MPV(fl) \approx 11.5 - 0.009 Plt_{PRE}(k/\mu l)$$

c. Ancillary Separation Efficiencies $\eta_{Anc}$ $\eta_{Anc}$ takes into account the efficiency (in terms of platelet loss) of other portions of the processing system. $\eta_{Anc}$ takes into account the efficiency of transporting platelets (in PRP) from the first stage chamber to the second stage chamber; the efficiency of transporting platelets (also in PRP) through the leukocyte removal filter; the efficiency of resuspension and transferral of platelets (in PC) from the second stage chamber after processing; and the efficiency of reprocessing previously processed blood in either a single needle or a double needle configuration.

The efficiencies of these ancillary process steps can be assessed based upon clinical data or estimated based upon computer modeling. Based upon these considerations, a predicted value for $\eta_{Anc}$ can be assigned, which Eq (5) treats as constant over the course of a given procedure.

2. Deriving Donor Platelet Count ($Plt_{Circ}$)

The utility function F1 relies upon a kinetic model to predict the donor's current circulating platelet count $Plt_{Circ}$ during processing. The model estimates the donor's blood volume, and then estimates the effects of dilution and depletion during processing, to derive $Plt_{Circ}$, according to the following relationships:

$$Plt_{Circ} = [(\text{Dilution}) \times Plt_{pre}] - (\text{Depletion})$$

where:

$Plt_{pre}$ is the donor's circulating platelet count before processing begins (k/μl), which can be measured by conventional techniques from a sample of whole blood taken from the donor before processing. There can be variations in $Plt_{pre}$ due to use of different counters (see, e.g., Peoples et al., "A Multi-Site Study of Variables Affecting Platelet Counting for Blood Component Quality Control," Transfusion (Special Abstract Supplement, 47th Annual Meeting), v. 34, No. 10S, October 1994 Supplement). The utility function therefore may include a look up table to standardize all platelet counts(such as, $Plt_{pre}$ and $Plt_{post}$, described later) for use by the function according to the type of counter used.

Dilution is a factor that reduces the donor's preprocessing circulating platelet count $Plt_{pre}$ due to increases in the donor's apparent circulating blood volume caused by the priming volume of the system and the delivery of anticoagulant. Dilution also takes into account the continuous removal of fluid from the vascular space by the kidneys during the procedure.

Depletion is a factor that takes into account the depletion of the donor's available circulating platelet pool by processing. Depletion also takes into account the counter mobilization of the spleen in restoring platelets into the circulating blood volume during processing.

a. Estimating Dilution

The utility function F1 estimates the dilution factor based upon the following expression:

$$\text{Dilution} = 1 - \frac{\text{Prime} + \frac{2ACD}{3} - PPP}{DonVol} \quad \text{Eq (12)}$$

where:

Prime is the priming volume of the system (ml).

ACD is the volume of anticoagulant used (current or end-point, depending upon the time the derivation is made)(ml).

PPP is the volume of PPP collected (current or goal) (ml).

DonVol (ml) is the donor's blood volume based upon models that take into account the donor's height, weight, and sex. These models are further simplified using empirical data to plot blood volume against donor weight linearized through regression to the following, more streamlined expression:

$$DonVol = 1024 + 51 Wgt (r^2 = 0.87) \quad \text{Eq (13)}$$

where:

Wgt is the donor's weight (kg).

b. Estimating Depletion

The continuous collection of platelets depletes the available circulating platelet pool. A first order model predicts that the donor's platelet count is reduced by the platelet yield (Yld) (current or goal) divided by the donor's circulating blood volume (DonVol), expressed as follows:

$$Depl = \frac{100{,}000 \, Yld}{DonVol} \quad \text{Eq (14)}$$

where:

Yld is the current instantaneous or goal platelet yield (k/µl). In Eq (14), Yld is multiplied by 100,000 to balance units.

Eq (14) does not take into account splenic mobilization of replacement platelets, which is called the splenic mobilization factor (or Spleen). Spleen indicates that donors with low platelets counts nevertheless have a large platelet reserve held in the spleen. During processing, as circulating platelets are withdrawn from the donor's blood, the spleen releases platelets it holds in reserve into the blood, thereby partially offsetting the drop in circulating platelets. The inventor has discovered that, even though platelet precounts vary over a wide range among donors, the total available platelet volume remains remarkably constant among donors. An average apparent donor volume is 3.10±0.25 ml of platelets per liter of blood. The coefficient of variation is 8.1%, only slightly higher than the coefficient of variation in hematocrit seen in normal donors.

The mobilization factor Spleen is derived from comparing actual measured depletion to Depl (Eq (14)), which is plotted and linearized as a function of $Plt_{pre}$. Spleen (which is restricted to a lower limit of 1) is set forth as follows:

$$Spleen = [2.25 - 0.004 Plt_{pre}] \geq 1 \quad \text{Eq (15)}$$

Based upon Eqs (14) and (15), the utility function derives Depletion as follows:

$$Depletion = \frac{100{,}000 \, Yld}{Spleen \times DonVol} \quad \text{Eq (16)}$$

3. Real Time Procedure Modifications

The operator will not always have a current platelet pre-count $Plt_{pre}$ for every donor at the beginning of the procedure. The utility function F1 allows the system to launch under default parameters, or values from a previous procedure. The utility function F1 allows the actual platelet pre-count $Plt_{Pre}$, to be entered by the operator later during the procedure. The utility function F1 recalculates platelet yields determined under one set of conditions to reflect the newly entered values. The utility function F1 uses the current yield to calculate an effective cleared volume and then uses that volume to calculate the new current yield, preserving the platelet pre-count dependent nature of splenic mobilization.

The utility function F1 uses the current yield to calculate an effective cleared volume as follows:

$$ClrVol = \frac{100{,}000 \times DonVol \times Yld_{Current}}{\left[DonVol - \text{Prime} - \frac{ACD}{3} + \frac{PPP}{2}\right] \times Pre_{Old} - \frac{50{,}000 \times Yld_{current}}{Spleen_{Old}}} \quad \text{Eq (17)}$$

where:

ClrVol is the cleared plasma volume.

DonVol is the donor's circulating blood volume, calculated according to Eq (13).

$Yld_{Current}$ is the current platelet yield calculated according to Eq (3) based upon current processing conditions.

Prime is the blood-side priming volume (ml).

ACD is the volume of anticoagulant used (ml).

PPP is the volume of platelet-poor plasma collected (ml).

$Pre_{Old}$ is the donor's platelet count before processing entered before processing begun (k/µl).

$Spleen_{Old}$ is the splenic mobilization factor calculated using Eq (16) based upon $Pre_{Old}$.

The utility function F1 uses ClrVol calculated using Eq (17) to calculate the new current yield as follows:

$$Yld_{New} = \left[\frac{DonVol - \text{Prime} - \frac{ACD}{3} + \frac{PPP}{2}}{DonVol + \frac{ClrVol}{2 \times Spleen_{New}}}\right] \times \left[\frac{ClrVol \times Pre_{New}}{100{,}000}\right] \quad \text{Eq (18)}$$

where:

$Pre_{New}$ is the revised donor platelet pre-count entered during processing (k/µl).

$Yld_{New}$ is the new platelet yield that takes into account the revised donor platelet pre-count $Pre_{New}$.

ClrVol is the cleared plasma volume, calculated according to Eq (17).

DonVol is the donor's circulating blood volume, calculated according to Eq (13), same as in Eq (17).

Prime is the blood-side priming volume (ml), same as in Eq (17).

ACD is the volume of anticoagulant used (ml), same as in Eq (17).

PPP is the volume of platelet-poor plasma collected (ml), same as in Eq (17).

$Spleen_{New}$ is the splenic mobilization factor calculated using Eq (15) based upon $Pre_{New}$.

4. Remaining Procedure Time

The utility function F2 can also calculate remaining collection time ($t_{rem}$) (in min) as follows:

$$t_{rem} = \frac{Vb_{rem}}{Q_b} \quad \text{Eq (19)}$$

where:

$Vb_{rem}$ is the remaining volume to be processed, calculated using Eq (19) based upon current processing conditions.

Qb is the whole blood flow rate, which is either set by the user or otherwise derived by the controller 18.

5. Plasma Collection

The utility function F2 adds the various plasma collection requirements to derive the plasma collection volume ($PPP_{Goal}$) (in ml) as follows:

$$PPP_{Goal} = PPP_{PC} + PPP_{Source} + PPP_{Reinfuse} + PPP_{waste} + PPP_{CollCham}$$

where:

$PPP_{PC}$ is the platelet-poor plasma volume selected for the PC product, which can have a typical default value of 250 ml, or be otherwise calculated by the controller 18 based upon current processing conditions.

$PPP_{Soure}$ is the platelet-poor plasma volume selected for collection as source plasma.

$PPP_{Waste}$ is the platelet-poor plasma volume selected to be held in reserve for various processing purposes (Default 30 ml).

$PPP_{CollCham}$ is the volume of the plasma collection chamber (Default=40 ml).

$PPP_{Reinfuse}$ is the platelet-poor plasma volume that will be reinfusion during processing.

6. Plasma Collection Rate

The utility function F2 calculates the plasma collection rate ($Q_{PPP}$) (in ml/min) as follows:

$$Q_{PPP} = \frac{PPP_{Goal} - PPP_{Current}}{t_{rem}} \quad \text{Eq (21)}$$

where:

$PPP_{Goal}$ is the desired platelet-poor plasma collection volume (ml).

$PPP_{Current}$ is the current volume of platelet-poor plasma collected (ml).

$t_{rem}$ is the time remaining in collection, calculated using Eq (19) based upon current processing conditions.

7. Total Anticipated AC Usage

The utility function F2 can also calculate the total volume of anticoagulant expected to be used during processing ($ACD_{End}$) (in ml) as follows:

$$ACD_{End} = ACD_{Current} + \frac{Q_b \times t_{rem}}{1 + AC} \quad \text{Eq (22)}$$

where:

$ACD_{Current}$ is the current volume of anticoagulant used (ml).

AC is the selected anticoagulant ratio,

Qb is the whole blood flow rate, which is either set by the user or otherwise calculated by the controller 18 based upon current processing conditions.

$t_{rem}$ is the time remaining in collection, calculated using Eq (19) based upon current processing conditions.

Various features of the inventions are set forth in the following claims.

We claim:

1. A blood processing system comprising
   a blood processing circuit including an element to separate blood drawn from a donor into at least one targeted blood component, a first container to collect a volume of the targeted blood component, and a second container to dispense a volume of a fluid,
   a controller including an input to receive from an operator a desired collection volume for the first container and a desired dispensing volume for the second container, the controller including a first utility function operating to perform a desired blood collection procedure including the steps of conveying blood from the donor through the blood processing circuit, separating the targeted blood component from the blood, collecting a volume of the targeted blood component in the first container, and conveying a volume the fluid from the second container to the donor, the controller including a second utility function operating to derive an estimated effect of the procedure upon the donor by calculating an estimated post-procedure intravascular blood volume deficit for the donor as a function of the desired collection volume for the first container and the desired dispensing volume for the second container, and
   an output to present the estimated effect to an operator.

2. A blood processing system comprising
   a blood processing circuit having a residual fluid volume and including an element to separate blood drawn from a donor into at least one targeted blood component and a container to collect a volume of the targeted blood component,
   a controller including an input to receive from an operator a desired collection volume for the container, the controller including a first utility function operating to perform a desired blood collection procedure including the steps of conveying blood from the donor through the blood processing circuit separating the targeted blood component from the blood, collecting a volume of the targeted blood component in the first container, and conveying a volume the replacement fluid from the second container to the donor, the controller including a second utility function operating to derive an estimated effect of the procedure upon the donor by calculating an estimated post-procedure intravascular blood volume deficit for the donor as a function of the desired collection volume for the container and the residual fluid volume of the blood processing circuit, and
   an output to present the estimated effect to an operator.

3. A blood processing system comprising
   a blood processing circuit having a residual fluid volume and including an element to separate blood drawn from a donor into at least one targeted blood component, a first container to collect a volume of the targeted blood component, and a second container to dispense a volume of a fluid,
   a controller including an input to receive from an operator a desired collection volume for the first container and a desired dispensing volume for the second container, the controller including a first utility function operating to perform a desired blood collection procedure including the steps of conveying blood from the donor through the blood processing circuit, separating the targeted blood component from the blood, collecting a volume of the targeted blood component in the first container, and conveying a volume the fluid from the second container to the donor, the controller including a second utility function operating to derive an estimated effect of the procedure upon the donor by calculating an estimated post-procedure intravascular blood volume deficit for the donor as a function of the desired collection volume for the first container, the desired dispensing volume for the second container, and the residual fluid volume of the blood processing circuit, and an output to present the estimated effect to an operator.

4. A blood processing system according to claim 1 or 3 wherein the fluid dispensed from the second container includes an anticoagulant.

5. A blood processing system according to claim 1 or 3 wherein the fluid dispensed from the second container includes fluid conveyed to the donor as a result of priming the blood processing circuit.

6. A blood processing system according to claim 1 or 2 or 3
wherein the second utility function operates by dividing the calculated estimated post-procedure intravascular blood volume deficit by a blood volume of the donor that existed prior to the desired blood processing procedure.

7. A blood processing system according to claim 1 or 2 or 3
wherein the second utility function operates by dividing the calculated estimated post-procedure intravascular blood volume deficit by weight of the donor.

8. A blood processing system according to claim 1 or 2 or 3
wherein the second utility function operates by calculating a post-procedure hematocrit of the donor as a function of the calculated estimated post-procedure intravascular blood volume deficit.

9. A blood processing system according to claim 1 or 2 or 3
wherein the desired collection volume comprises a volume of red blood cells.

10. A blood processing system according to claim 1 or 2 or 3
wherein the desired collection volume comprises a volume of platelets.

11. A blood processing system according to claim 1 or 2 or 3
wherein the desired collection volume comprises a volume of plasma.

12. A blood processing system according to claim 1 or 2 or 3
wherein the desired collection volume comprises a volume of platelets and a volume of red blood cells.

13. A system according to claim 1 or 2 or 3
wherein the output presents the estimated effect in a visual display.

14. A system according to claim 1 or 2 or 3
wherein the output presents the estimated effect in printed form.

15. A system according to claim 1 or 2 or 3
wherein the output presents the estimated effect in a data form suitable for offloading.

16. A blood processing method comprising the steps
establishing a blood processing circuit including an element to separate blood drawn from a donor into at least one targeted blood component, a first container to collect a volume of the targeted blood component, and a second container to dispense a volume of a fluid,
designating a desired collection volume for the first container,
designating a desired dispensing volume for the second container,
performing a desired blood collection procedure by conveying blood from the donor through the blood processing circuit, separating the targeted blood component from the blood, collecting a volume of the targeted blood component in the first container, and conveying a volume the fluid from the second container to the donor,
deriving an estimated effect of the procedure upon the donor by calculating an estimated post-procedure intravascular blood volume deficit for the donor as a function of the desired collection volume for the first container and the desired dispensing volume for the second container, and
presenting the estimated effect to an operator.

17. A blood processing method comprising the steps of
establishing a blood processing circuit having a residual volume and including an element to separate blood drawn from a donor into at least one targeted blood component and a container to collect a volume of the targeted blood component,
designating a desired collection volume for the first container,
performing a desired blood collection procedure by conveying blood from the donor through the blood processing circuit, separating the targeted blood component from the blood, and collecting a volume of the targeted blood component in the container,
deriving an estimated effect of the procedure upon the donor by calculating an estimated post-procedure intravascular blood volume deficit for the donor as a function of the desired collection volume for the first container and the residual fluid volume of the blood processing circuit, and
presenting the estimated effect to an operator.

18. A blood processing method according to claim comprising the steps of
establishing a blood processing circuit having a residual fluid volume and including an element to separate blood drawn from a donor into at least one targeted blood component, a first container to collect a volume of the targeted blood component, and a second container to dispense a volume of a fluid,
designating a desired collection volume for the first container,
designating a desired dispensing volume for the second container,
performing a desired blood collection procedure by conveying blood from the donor through the blood processing circuit, separating the targeted blood component from the blood, collecting a volume of the targeted blood component in the first container, and conveying a volume of the fluid from the second container to the donor, and
deriving an estimated effect of the procedure upon the donor by calculating an estimated post-procedure intravascular blood volume deficit for the donor as a function of the desired collection volume for the first container, the desired dispensing volume of the second container and the residual fluid volume of the blood processing circuit, and
presenting the estimated effect to an operator.

19. A method according to claim 16 or 18
wherein the fluid conveyed from the second container includes an anticoagulant.

20. A method according to claim 16 or 18
wherein the fluid conveyed from the second container includes a volume of priming fluid conveyed to the donor as a result of priming the blood processing circuit.

21. A method according to claim 16 or 17 or 18 wherein the deriving step includes the step of dividing the calculated estimated post-procedure intravascular blood volume deficit by a blood volume of the donor that existed prior to the desired blood processing procedure.

22. A method according to claim 16 or 17 or 18 wherein the deriving step includes the step of dividing the calculated estimated post-procedure intravascular blood volume deficit by weight of the donor.

23. A blood processing method according to claim 16 or 17 or 18 wherein the deriving step includes the step of calculating a post-procedure hematocrit of the donor as a function of the calculated estimated post-procedure intravascular blood volume deficit.

24. A method according to claim 16 or 17 or 18 wherein the desired collection volume comprises a volume of red blood cells.

25. A method according to claim 16 or 17 or 18 wherein the desired collection volume comprises a volume of platelets.

26. A method according to claim 16 or 17 or 18 wherein the desired collection volume comprises a volume of plasma.

27. A method according to claim 16 or 17 or 18 wherein the desired collection volume comprises a volume of red blood cells and a volume of platelets.

28. A method according to claim 16 or 17 or 18 wherein the presenting step comprises presenting the estimated effect in a visual display.

29. A method according to claim 16 or 17 or 18 wherein the presenting step comprises presenting the estimated effect in printed form.

30. A method according to claim 16 or 17 or 18 wherein the presenting step comprises presenting the estimated effect in a data form suitable for offloading.

* * * * *